(12) United States Patent
Fabrega et al.

(10) Patent No.: US 8,216,800 B2
(45) Date of Patent: Jul. 10, 2012

(54) SUBSTRATES FOR DETECTING PEPTIDASE ACTIVITY AND METHODS USING THE SUBSTRATES

(75) Inventors: Olivier Fabrega, Newcastle Upon Tyne (GB); Arthur James, Cumbria (GB); Vindhya Lakshika Salwatura, Newcastle Upon Tyne (GB); Sylvain Orenga, Neuville sur Ain (FR); Stephen Stanforth, Northumberland (GB)

(73) Assignee: Biomerieux, Marcy L'Etoile (FR)

( * ) Notice: Subject to any disclaimer, the term of this patent is extended or adjusted under 35 U.S.C. 154(b) by 244 days.

(21) Appl. No.: 12/451,291

(22) PCT Filed: May 29, 2008

(86) PCT No.: PCT/FR2008/050936
§ 371 (c)(1), (2), (4) Date: Nov. 5, 2009

(87) PCT Pub. No.: WO2008/152306
PCT Pub. Date: Dec. 18, 2008

(65) Prior Publication Data
US 2010/0099128 A1 Apr. 22, 2010

(30) Foreign Application Priority Data
May 31, 2007 (FR) ...................................... 07 55371

(51) Int. Cl.
*C12Q 1/37* (2006.01)
(52) U.S. Cl. ........................................................ 435/24
(58) Field of Classification Search ...................... 435/24
See application file for complete search history.

(56) References Cited

U.S. PATENT DOCUMENTS

| | | | |
|---|---|---|---|
| 6,046,016 A | 4/2000 | Orenga | |
| 6,905,841 B2 * | 6/2005 | Desmonceaux et al. | 435/34 |
| 2005/0272765 A1 | 12/2005 | Feng et al. | |
| 2010/0028926 A1 * | 2/2010 | Anderson et al. | 435/24 |

FOREIGN PATENT DOCUMENTS

| | | |
|---|---|---|
| FR | 2 751 663 A1 | 1/1998 |
| WO | WO 98/04735 A1 | 2/1998 |
| WO | WO 99/38995 A1 | 8/1999 |
| WO | WO 2006/030119 A1 | 3/2006 |

OTHER PUBLICATIONS

Different Chemical Libraries Suppliers, Database Registry STN, Mar. 15, 2007, XP002465502, compounds described in Registry between Dec. 2002 and Oct. 2007.
Manafi et al., "Fluorogenic and Chromogenic Substrates Used in Bacterial Diagnostics," *Microbiological Reviews*, Sep. 1991, pp. 335-348, vol. 55, No. 3, American Society for Microbiology, USA.
Dikov et al., "New Fluorogenic Substrates in Histochemistry of Peptidases: I. Histochemical Determination of Alanineaminopeptidase," *Report of the Bulgarian Academy of Science*, 1996, pp. 89-92, vol. 49, No. 4, Institute of Experimental Morphology and Anthropology, Bulgaria.
International Search Report issued in International Application No. PCT/FR2008/050936 on May 14, 2009.

* cited by examiner

*Primary Examiner* — Ralph Gitomer
(74) *Attorney, Agent, or Firm* — Oliff & Berridge, PLC

(57) ABSTRACT

An enzyme substrate of formula (I) detects peptidase activity:

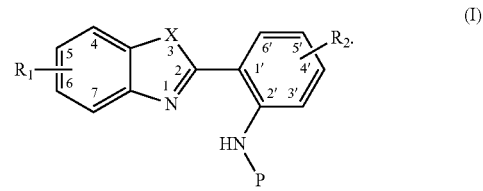

Methods of detecting peptidase activity of a microorganism may include incubating a biological sample with the enzyme substrate of formula (I), and detecting peptidase activity if a microorganism having peptidase activity is present in the biological sample. The enzyme substrate may be included in a reaction medium.

21 Claims, No Drawings

SUBSTRATES FOR DETECTING PEPTIDASE ACTIVITY AND METHODS USING THE SUBSTRATES

This application is a National Stage application filed under 371 based upon PCT/FR2008/050936 May 29, 2008 which claims priority to Application France 0755371 filed May 31, 2007.

The present invention relates to novel enzyme substrates for detecting peptidase activity. These substrates can be used in applications comprising a step of enzymatic hydrolysis producing a physicochemical signal, in particular in microbiology, biochemistry, immunology, molecular biology, histology, etc. The invention also relates to reaction media containing such substrates, to the use of the substrates or of the media for detecting peptidase activities and/or for distinguishing Gram-positive bacteria from Gram-negative bacteria, and to methods of use.

A very large number of media currently exist for detecting microorganisms. This detection can be based especially on the use of particular substrates specific for an enzyme of the microorganism that it is desired to detect. In general, synthetic substrates for enzymes are constituted of a first part specific for the enzymatic activity to be revealed, and a second part which acts as a label, generally a chromogenic or fluorescent label. Thus, in the case of bacteria, by virtue of the choice of substrates, depending on whether or not there is a reaction, it is possible to characterize the nature of a microorganism. A peptidase activity can in particular be used to reveal a group, a genus or a species of bacteria. Thus, alanine aminopeptidase activity, for example, makes it possible to differentiate between Gram-negative bacteria and Gram-positive bacteria.

Chromogenic enzyme substrates for detecting peptidase activity are known from the prior art. Mention may in particular be made of the publication by Manafi (Manafi et al, Microbiol Rev 55(3): 335-348, 1991), which is a review of enzyme substrates used in microbiology. However, the aminopeptidase substrates described release, by hydrolysis, compounds that diffuse in the medium (beta-naphthylamine, 7-amino-4-methylcoumarin). As a result, in a heterogeneous reaction medium (colonies on Petri dishes, histological section, etc.), it is not possible to precisely localize the site of hydrolysis. Mention may also be made of the substrates described in patent applications WO 98/04735 and WO 99/38995 filed by the applicant. However, although these substrates do not diffuse a great deal in culture medium, they have certain drawbacks: they are difficult to synthesize, the purity is low, the yields are low and they are toxic with respect to certain microorganisms.

The present invention therefore proposes novel peptidase substrates for detecting microorganisms. Compared with the existing substrates, these novel substrates are easy to synthesize and can be used in particular in gelled media for detecting microorganisms, since they produce a coloration which does not diffuse in the reaction medium. This makes it possible to pinpoint a colony or an organelle expressing peptidase activity, among others not expressing it.

Before proceeding with the description of the invention, the definitions below are given in order to facilitate the disclosure of the invention.

The term enzyme substrate is intended to mean a substrate that can be hydrolyzed by an enzyme so as to give a product which allows the direct or indirect detection of a microorganism, of a cell or of an organelle. This substrate comprises in particular a first part specific for the enzymatic activity to be revealed and a second part which acts as a label.

The substrates according to the invention are particularly suitable for use in flow cytometry because, since the product of hydrolysis remains mainly localized in the cell expressing the enzymatic activity, it is possible to specifically count the cells expressing this activity, or even to separate them from the rest of the sample.

The substrates according to the invention are also highly suitable for use in histoenzymology because, since the product of hydrolysis remains mainly localized on the site of hydrolysis, it is possible to specifically identify the cells or organelles expressing this activity within a tissue.

Owing to their low toxicity, the substrates according to the invention are highly suitable for monitoring cell culture peptidase activity.

The substrates according to the invention are also very suitable for use in a detection and/or identification medium since they produce a coloration or a fluorescence which does not diffuse in the reaction medium. In the present application, the term "coloration" is used to cover a coloration, which is absorption of light in the visible spectrum, or a fluorescence, which is absorption at one wavelength ($\lambda_{ex}$) and emission at a higher wavelength a ($\lambda_{em}$, $\lambda_{em} > \lambda_{ex}$).

The substrates of the invention may be salified, i.e. in the form of a salt such as chloride, bromide or trifluoroacetate.

The term peptidase is intended to mean an enzyme capable of cleaving, by hydrolysis, the amide group formed between the acyl residue of a peptide and a primary amine. The term aminopeptidase is intended to mean an enzyme capable of cleaving, by hydrolysis, the amide group formed between an amino acid acyl and a primary amine. In the present application, the term "peptidase" can denote, as appropriate, both a peptidase and an aminopeptidase as defined above.

The term peptide is intended to mean a peptide chain comprising from 1 to 10 amino acids, preferably from 1 to 4 amino acids. Preferably, the peptide is di-alanine or tri-alanine. The term amino acid is intended to mean any natural or unnatural amino acid known to those skilled in the art. According to one particular embodiment of the invention, the amino acid is a beta-alanine or L-alanine, or a glycine, pyrroglutamyl, etc.

Said peptide may comprise a blocking agent at its N-terminal end. The blocking agents according to the invention comprise any blocking agent known to those skilled in the art which is capable of protecting amines. By way of example, mention may be made of t-butoxycarbonyl (N-tBOC), 9-fluorenyloxycarbonyl, a solubilizing agent such as succinyl, or else a nonmetabolizable amino acid, i.e. an unnatural amino acid, such as pipecolic acid or the D form of an amino acid, such as D-phenylalanine. The blocking agents are not systematically present in the compounds of the invention.

The term alkyl group is intended to mean a chain of saturated hydrocarbon-based groups, such as, in particular, a $C_1$-$C_6$ alkyl, i.e. a straight or branched alkyl containing from 1 to 6 carbon atoms. By way of example, mention may be made of methyl, ethyl, propyl, isopropyl, butyl, t-butyl, pentyl, isopentyl and hexyl.

The term aryl group is intended to mean a functional group (or substituent) which derives from an aromatic ring, for instance a $C_6$-$C_{10}$ aromatic ring, in particular phenyl, benzyl, 1-naphthyl or 2-naphthyl.

The term carboxyl group is intended to mean in particular a functional group composed of a carbon atom, linked via a double bond to a first oxygen atom, and via a single bond to a second oxygen atom, itself negatively charged or linked to a hydrogen atom.

Depending on the $pK_a$ of the molecule and of the pH of the medium, the carboxyl group may be in ionized form, i.e. without H linked to the second oxygen atom, which is then negatively charged.

The term reaction medium is intended to mean a medium comprising all the elements necessary for the expression of a metabolism and/or for the growth of microorganisms, of a cell or of an organelle. This reaction medium can be used in flow cytometry, histoenzymology, cell culture, etc., or as a microorganism detection and/or identification medium.

The reaction medium may comprise one or more elements in combination, such as amino acids, peptones, carbohydrates, nucleotides, minerals, vitamins, antibiotics, surfactants, buffers, phosphate salts, ammonium salts, sodium salts or metal salts.

The medium may also comprise a colorant. By way of indication, mention may be made, as colorant, of Evans blue, neutral red, sheep blood, horse blood, an opacifier such as titanium oxide, nitroaniline, malachite green, brilliant green, etc.

The reaction medium may be solid, semi-solid or liquid. The term "solid medium" is intended to mean, for example, a gelled medium. Agar is the conventional gelling agent in microbiology for culturing microorganisms, but it is possible to use gelatine or agarose. A certain number of preparations are commercially available, for instance Columbia agar, trypticase-soy agar, MacConkey agar, Sabouraud agar, or more generally those described in the Handbook of Microbiological Media (CRC Press).

The reaction medium may be a detection and/or identification medium, i.e. a developing medium or a culture and developing medium. In the first case, the microorganisms are cultured before inoculation, and in the second case, the detection and/or identification medium also constitutes the culture medium.

The term biological sample is intended to mean a clinical sample, derived from a biological fluid specimen, or a food sample, derived from any type of food. This sample may thus be liquid or solid and mention may be made, without limitation, of a clinical sample of blood, plasma, urine or feces, or of specimens from the nose, throat, skin, a wound or cerebrospinal fluid, a food sample from water or from a drink such as milk or a fruit juice; from yoghourt, from meat, from eggs, from vegetables, from mayonnaise, from cheese; from fish, etc., or a food sample derived from an animal feed, such as in particular a sample derived from animal meal. The sample may also be a specimen from the clinical environment, a livestock specimen or a specimen from food, cosmetic or pharmaceutical production. The term "environment specimen" is intended to mean in particular a specimen taken from a surface, from a liquid, from a starting material or from a product.

For the purpose of the present invention, the term microorganism covers bacteria, yeasts and, more generally, organisms that are generally single-cell, invisible to the naked eye, and that can be multiplied and manipulated in the laboratory.

By way of Gram-negative bacteria, mention may be made of the bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*.

By way of Gram-positive bacteria, mention may be made of the bacteria of the following genera: *Aerococcus, Enterococcus, Streptococcus, Staphylococcus, Bacillus, Lactobacillus, Listeria, Clostridium, Gardnerella, Kocuria, Lactococcus, Leuconostoc, Micrococcus, Falkamia, Gemella, Pediococcus, Mycobacterium* and *Corynebacterium*.

By way of yeasts, mention may be made of the yeasts of the following genera: *Candida, Cryptococcus, Saccharomyces* and *Trichosporon*.

The invention relates to an enzyme substrate for detecting peptidase activity, of formula (I) below:

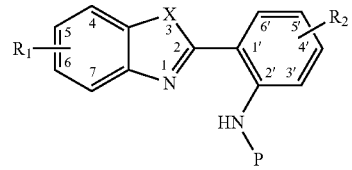

in which:
X is S; NX1; O; or NX1-CO;
R1 is nothing or one of the following substituents: Cl, Br, F, I, OH, or an alkyl, aryl or carboxyl group;
R2 is nothing or one of the following substituents: Cl; O—$CH_2$—O; O—$CH_3$; F, diethylenediamine-$CH_3$, NR3R4, Br, I, OH, an alkyl, aryl or carboxyl group, $NO_2$, or

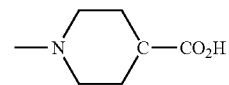

X1 is selected from H, $C_2H_4Ph$, OH, an alkyl group and an aryl group;
R3 and R4 are independently H or an alkyl group containing from 1 to 4 carbon atoms;
P is a peptide.

The bond between the nitrogen in the 1-position and the carbon in the 2-position on the heterocycle may be single (1,2-dihydro) or double, preferably double.

Of course, the substrate according to the invention may comprise several substituents, i.e. several R1 and R2 groups in various positions on the ring. When R1 and/or R2 is an alkyl or aryl group, it may also be substituted with one or more substituents such as OH, carboxyl, Br, Cl, F or I. When R2 is O—$CH_2$—O, R2 is a ring fused to the aminophenyl, two of their ring members being shared.

According to a first alternative, when X is NX1-CO, the ring comprising X is a 6-membered ring, comprising an O in the 3-position and NX1 in the 4-position of said 6-membered ring.

According to a second alternative, when X is NX1-CO, the ring comprising X is a 6-membered ring, comprising NX1 in the 3-position and a C linked via a double bond to an O in the 4-position of said 6-membered ring.

According to one preferred embodiment of the invention, X is S.

According to another preferred embodiment of the invention, X is N—X1.

According to another preferred embodiment of the invention, X is O.

According to another preferred embodiment of the invention, X is NX1-CO.

According to one particular embodiment of the invention, R1 is in the 5-position.

According to one particular embodiment of the invention, R2 is in the 4'-position.

According to another particular embodiment of the invention, R2 is in the 5'-position.

According to another particular embodiment of the invention, R2 is in the 4'-position and in the 5'-position.

According to one particular embodiment of the invention, P comprises a blocking agent at its N-terminal end.

According to one particular embodiment of the invention, said enzyme substrate corresponds to formula (I) as defined above and in which:
X is O;
R1 and R2 are nothing;
P is a peptide, preferably an amino acid, preferably selected from a beta-alanine, an L-alanine and a glycine.

According to one particular embodiment of the invention, said enzyme substrate corresponds to formula (I) above, X is O, R1 and R2 are nothing, and P is a beta-alanine.

According to another particular embodiment of the invention, said enzyme substrate corresponds to formula (I) above, X is O, R1 and R2 are nothing and P is L-alanine.

According to another particular embodiment of the invention, said enzyme substrate corresponds to formula (I) above, X is O, R1 and R2 are nothing and P is a glycine.

According to another particular embodiment of the invention, said enzyme substrate corresponds to formula (I) as defined above and in which:
X is O;
R1 is Cl;
R2 is nothing;
P is a peptide.

Preferably, P is an amino acid, preferably an L-alanine. Preferably, R1 is in the 5-position.

According to one particular embodiment of the invention, said enzyme substrate corresponds to formula (I) above, X is O, R1 is Cl in the 5-position, R2 is nothing, and P is an L-alanine.

According to one particular embodiment of the invention, said enzyme substrate corresponds to formula (I) as defined above and in which:
X is O;
R1 is $CH_3$;
R2 is nothing;
P is a peptide, preferably an amino acid, preferably L-alanine.

According to one particular embodiment of the invention, said enzyme substrate corresponds to formula (I) above, X is O, R1 is $CH_3$ in the 5-position, R2 is nothing, and P is L-alanine.

According to one particular embodiment of the invention, said enzyme substrate corresponds to formula (I) as defined above and in which:
X is O;
R1 is nothing;
R2 is Cl;
P is a peptide, preferably an amino acid, preferably L-alanine or beta-alanine.

According to one particular embodiment of the invention, said enzyme substrate corresponds to formula (I) above, X is O, R1 is nothing, R2 is Cl in the 5'-position, and P is L-alanine.

According to one particular embodiment of the invention, said enzyme substrate corresponds to formula (I) above, X is O, R1 is nothing, R2 is Cl in the 5'-position, and P is beta-alanine.

According to one particular embodiment of the invention, said enzyme substrate corresponds to formula (I) as defined above and in which:
X is O;
R1 is nothing;
R2 is O—$CH_2$—O;
P is a peptide, preferably an amino acid, preferably selected from L-alanine and beta-alanine.

According to one particular embodiment of the invention, said enzyme substrate corresponds to formula (I) above, X is O, R1 is nothing, R2 is O—$CH_2$—O, fused to the aminocycle in the 4'- and 5'-position, and P is L-alanine.

According to one particular embodiment of the invention, said enzyme substrate corresponds to formula (I) above, X is O, R1 is nothing, R2 is O—$CH_2$—O, fused to the aminocycle in the 4'- and 5'-position, and P is beta-alanine.

According to another particular embodiment of the invention, said enzyme substrate corresponds to formula (I) as defined above and in which:
X is O;
R1 is nothing;
R2 is O—$CH_3$;
P is a peptide.

Preferably, P is an amino acid, preferably a beta-alanine or an L-alanine. Preferably, R2 is in the 4'- and 5'-position.

According to one particular embodiment of the invention, said enzyme substrate corresponds to formula (I) above, X is O, R1 is nothing, R2 is O—$CH_3$ in the 4'- and 5'-position and P is a beta-alanine.

According to one particular embodiment of the invention, said enzyme substrate corresponds to formula (I) above, X is O, R1 is nothing, R2 is O—$CH_3$ in the 4'- and 5'-position, and P is an L-alanine.

According to another particular embodiment of the invention, said enzyme substrate corresponds to formula (I) as defined above and in which:
X is O;
R1 is nothing;
R2 is F;
P is a peptide.

Preferably, P is an amino acid, preferably a beta-alanine. Preferably, R2 is in the 5'-position.

According to one particular embodiment of the invention, said enzyme substrate corresponds to formula (I) above, X is O, R1 is nothing, R2 is F in the 5'-position, and P is a beta-alanine.

According to one particular embodiment of the invention, said enzyme substrate corresponds to formula (I) as defined above and in which:
X is NX1;
X1 is $CH_3$;
R1 and R2 are nothing;
P is a peptide, preferably an amino acid, preferably L-alanine.

According to one particular embodiment of the invention, said enzyme substrate corresponds to formula (I) above, X is NX1, X1 is $CH_3$, R1 and R2 are nothing, and P is L-alanine.

According to one particular embodiment of the invention, said enzyme substrate corresponds to formula (I) as defined above and in which:
X is NX1;
X1 is $C_2H_4Ph$;
R1 and R2 are nothing;
P is a peptide, preferably an amino acid, preferably L-alanine.

According to one particular embodiment of the invention, said enzyme substrate corresponds to formula (I) above, X is NX1, X1 is $C_2H_4Ph$, R1 and R2 are nothing, and P is L-alanine.

According to one particular embodiment of the invention, said enzyme substrate corresponds to formula (I) as defined above and in which:
X is NX1;
X1 is $C_2H_4Ph$;
R1 is nothing;
R2 is Cl;
P is a peptide, preferably an amino acid, preferably L-alanine.

According to one particular embodiment of the invention, said enzyme substrate corresponds to formula (I) above, X is NX1, X1 is $C_2H_4Ph$, R1 is nothing, R2 is Cl in the 5'-position, and P is L-alanine.

According to one particular embodiment of the invention, said enzyme substrate corresponds to formula (I) as defined above and in which:
X is NX1;
X1 is $C_2H_4Ph$;
R1 is nothing;
R2 is O—$CH_2$—O;
P is a peptide, preferably an amino acid, preferably selected from L-alanine and beta-alanine.

According to one particular embodiment of the invention, said enzyme substrate corresponds to formula (I) above, X is NX1, X1 is $C_2H_4Ph$, R1 is nothing, R2 is O—$CH_2$—O, fused to the aminocycle in the 4'- and 5'-position, and P is L-alanine.

According to one particular embodiment of the invention, said enzyme substrate corresponds to formula (I) above, X is NX1, X1 is $C_2H_4Ph$, R1 is nothing, R2 is O—$CH_2$—O, fused to the aminocycle in the 4'- and 5'-position, and P is beta-alanine.

According to another particular embodiment of the invention, said enzyme substrate corresponds to formula (I) above and in which:
X is S;
R1 is nothing;
R2 is nothing;
P is a peptide, preferably an amino acid, preferably selected from L-alanine or a beta-alanine.

According to one particular embodiment of the invention, said enzyme substrate corresponds to formula (I) above, X is S, R1 and R2 are nothing and P is L-alanine.

According to one particular embodiment of the invention, said enzyme substrate corresponds to formula (I) above, X is S, R1 and R2 are nothing and P is beta-alanine.

According to another particular embodiment of the invention, said enzyme substrate corresponds to formula (I) above and in which:
X is S;
R1 is nothing;
R2 is Cl;
P is a peptide.

Preferably, P is an amino acid, preferably L-alanine. Preferably, R2 is in the 5'-position.

According to one particular embodiment of the invention, said enzyme substrate corresponds to formula (I) above, X is S, R1 is nothing, R2 is Cl in the 5'-position, and P is L-alanine.

According to one particular embodiment of the invention, said enzyme substrate corresponds to formula (I) as defined above and in which:
X is S;
R1 is $CH_3$;
R2 is nothing;
P is a peptide, preferably an amino acid, preferably L-alanine.

According to one particular embodiment of the invention, said enzyme substrate corresponds to formula (I) above, X is S, R1 is $CH_3$ in the 5-position, R2 is nothing, and P is L-alanine.

According to one particular embodiment of the invention, said enzyme substrate corresponds to formula (I) as defined above and in which:
X is NX1-CO;
X1 is H;
R1 is nothing;
R2 is Cl;
P is a peptide, preferably an amino acid, preferably L-alanine.

According to one particular embodiment of the invention, said enzyme substrate corresponds to formula (I) above, X is NX1-CO, X1 is H, R1 is nothing, R2 is Cl in the 5'-position, and P is L-alanine.

According to one particular embodiment of the invention, said enzyme substrate corresponds to formula (I) as defined above and in which:
X is NX1-CO;
X1 is H;
R1 is nothing;
R2 is nothing;
P is a peptide, preferably an amino acid, preferably L-alanine.

According to one particular embodiment of the invention, said enzyme substrate corresponds to formula (I) above, X is NX1-CO, X1 is H, R1 is nothing, R2 is nothing, and P is L-alanine.

According to one particular embodiment of the invention, said enzyme substrate corresponds to formula (I) as defined above and in which:
X is NX1-CO;
X1 is $CH_3$;
R1 is nothing;
R2 is nothing;
P is a peptide, preferably an amino acid, preferably L-alanine.

According to one particular embodiment of the invention, said enzyme substrate corresponds to formula (I) above, X is NX1-CO, X1 is $CH_3$, R1 is nothing, R2 is nothing, and P is L-alanine.

Preferably, the substrate according to the invention is selected from the substrates described in Table 1.

TABLE 1

Examples of substrates according to the invention

| Substrates | Reference | X | X1 | R1 | R2 | P |
|---|---|---|---|---|---|---|
| 2-(L-Alanyl-2'-amidophenyl)-benzoxazole | Substrate 1 VLS206, 27 | O | — | — | — | L-Ala |
| 2-(β-Alanyl-2'-amidophenyl)-benzoxazole | Substrate 2 OF22A | O | — | — | — | β-Ala |

TABLE 1-continued

Examples of substrates according to the invention

| Substrates | Reference | X | X1 | R1 | R2 | P |
|---|---|---|---|---|---|---|
| 2-(Glycyl-2'-amidophenyl)-benzoxazole | Substrate 3 OF30B | O | — | — | — | Gly |
| 2-(2'-L-Alanylamidophenyl)-5-chlorobenzoxazole | Substrate 4 35 | O | — | Cl | — | L-Ala |
| 2-(L-Alanyl-2'-amidophenyl)-5-methylbenzoxazole | Substrate 5 | O | — | $CH_3$ | — | L-Ala |
| 2-(L-Alanyl-2'-amido-5'-chlorophenyl)benzoxazole | Substrate 6 VLS283 | O | — | — | Cl | L-Ala |
| 2-(β-Alanyl-2'-amido-5'-chlorophenyl)benzoxazole | Substrate 7 OF23A | O | — | — | Cl | β-Ala |
| 2-(L-Alanyl-2'-amido-4',5'-cyclomethylenedioxyphenyl)-benzoxazole | Substrate 8 | O | — | — | $O-CH_2-O$ | L-Ala |
| 2-(β-Alanyl-2'-amido-4',5'-cyclomethylenedioxyphenyl)-benzoxazole | Substrate 9 | O | — | — | $O-CH_2-O$ | β-Ala |
| 2-(L-Alanyl-2'-amido-4',5'-dimethoxyphenyl)benzoxazole | Substrate 10 VLS284 | O | — | — | $O-CH_3, O-CH_3$ | L-Ala |
| 2-(β-Alanyl-2'-amido-4',5'-dimethoxyphenyl)benzoxazole | Substrate 11 OF24A | O | — | — | $O-CH_3, O-CH_3$ | β-Ala |
| 2-(β-Alanyl-2'-amido-5'-fluorophenyl)benzoxazole | Substrate 12 OF28A | O | — | — | F | β-Ala |
| 2-(L-Alanyl-2'-amidophenyl)-3-methylbenzimidazole | Substrate 13 43 | NX1 | $CH_3$ | — | — | L-Ala |
| 2-(L-Alanyl-2'-amidophenyl)-3-phenylethylbenzimidazole | Substrate 14 57 | NX1 | $C_2H_4Ph$ | — | — | L-Ala |
| 2-(L-Alanyl-2'-amido-5'-chlorophenyl)-3-phenylethylbenzimidazole | Substrate 15 59 | NX1 | $C_2H_4Ph$ | — | Cl | L-Ala |
| 2-(L-Alanyl-2'-amido-4',5'-methylenedioxyphenyl)-3-phenylethylbenzimidazole | Substrate 16 60 | NX1 | $C_2H_4Ph$ | — | $O-CH_2-O$ | L-Ala |
| 2-(L-Alanyl-2'-amidophenyl)-benzothiazole | Substrate 17 OF38A | S | — | — | — | L-Ala |
| 2-(β-Alanyl-2'-amidophenyl)-benzothiazole | Substrate 18 OF33A | S | — | — | — | β-Ala |
| 2-(L-Alanyl-2'-amido-5'-chlorophenyl)benzothiazole | Substrate 19 | S | — | — | Cl | L-Ala |
| 2-(L-Alanyl-2'-amidophenyl)-5-methylbenzothiazole | Substrate 20 | S | — | $CH_3$ | — | L-Ala |
| 2-(L-Alanyl-2'-amido-5'-chlorophenyl)quinoxazol-4-one | Substrate 21 VLS289 | NX1-CO | H | — | Cl | L-Ala |
| 2-(L-Alanyl-2'-amidophenyl)-3-hydroquinazolin-4-one | Substrate 22 VLS298 | NX1-CO | H | — | — | L-Ala |
| 2-(L-Alanyl-2'-amidophenyl)-3-methylquinazoline-4-one | Substrate 23 VLS297 | NX1-CO | $CH_3$ | — | — | L-Ala |

The invention also relates to a reaction medium comprising at least one enzyme substrate as defined above.

Preferably, said reaction medium is a microorganism detection and/or identification medium, said medium comprising at least one enzyme substrate as defined above.

Preferably, said substrate is at a concentration of between 1 and 1000 mg/l, preferably between 10 and 500 mg/l.

According to one particular embodiment of the invention, said detection and/or identification medium according to the invention also comprises at least one other enzyme substrate, specific for an enzymatic activity different to that detected by the substrate according to the invention.

The enzymatic hydrolysis of the other substrate(s) generates a detectable signal, different to the signal detected via the substrate of the invention, for instance different colored or fluorescent products, so as to allow the demonstration, such as the detection and/or the identification and/or the quantification, of one or more microorganisms. By way of other specific substrate, use may be made of any other substrate conventionally used in the detection of microorganisms. The concentration of the other specific enzyme substrate is generally between 0.01 and 1 g/l. Those skilled in the art will be able to readily determine such a concentration as a function of the substrate used. By way of indication, it is possible to combine the substrates according to the invention with peptidase, osidase, esterase or reductase enzyme substrates. In particular, it is possible to combine a substrate according to the invention for which P is a β-alanine, with an osidase substrate, such as 5-bromo-4-chloro-3-indolyl-β-glucoside, or alizarin-β-galactoside. It is also possible to combine a substrate according to the invention for which P is L-alanine, with an esterase substrate, such as 5-bromo-6-chloro-3-indoxyl octanoate or 5-bromo-3-indoxyl phosphate.

According to one particular embodiment of the invention, said detection and/or identification medium according to the invention also comprises at least one other enzyme substrate specific for the enzymatic activity detected by the substrate according to the invention. Through the particular choice of substrates, it is then possible to identify groups of microorganisms expressing the same enzymatic activity. The concentration of the other specific enzyme substrate is generally between 0.01 and 1 g/l. Those skilled in the art will be able to readily determine such a concentration as a function of the substrate used. In particular, it is possible to combine a substrate according to the invention for which P is an L-alanine, with a substrate for L-alanine aminopeptidase described in application WO2006030119, such as L-alaninepentylresorufamine.

The invention also relates to the use of enzyme substrates as defined above or of a detection and/or identification medium as defined above, for detecting at least one peptidase activity in microorganisms.

The invention also relates to the use of enzyme substrates as defined above or of a detection and/or identification medium as defined above, for separating Gram-positive bacteria from Gram-negative bacteria.

The invention also relates to a method for detecting at least one peptidase activity in microorganisms, characterized in that it comprises or is constituted of the following steps:

a) providing a detection and/or identification medium as defined above, b) inoculating the medium with a biological sample to be tested, c) leaving this to incubate, and d) revealing the presence of at least one peptidase activity.

The inoculating of the microorganisms can be carried out by any of the inoculation techniques known to those skilled in the art. An incubation step may be carried out at a temperature for which the expression of the enzymatic activity that it is desired to detect is optimal, and which those skilled in the art can readily select according to the enzymatic activity to be detected. Step d) can be carried out by visual examination, or by colorimetry or fluorimetry. During step d), it is possible to reveal the presence of the peptidase activity alone or in combination with at least one other enzymatic activity.

The invention also relates to a method for differentiating bacteria in terms of whether they belong to Gram-positive bacteria or to Gram-negative bacteria, characterized in that it comprises or is constituted of the following steps:

a) providing a detection and/or identification medium as defined above, b) inoculating the medium with a biological sample to be tested, c) leaving this to incubate, and d) revealing the presence of at least one peptidase activity.

As indicated above, the inoculating of the microorganisms can be carried out by any of the inoculation techniques known to those skilled in the art. An incubation step can be carried out at a temperature for which the expression of the enzymatic activity that it is desired to detect is optimal, and which those skilled in the art can readily select according to the enzymatic activity to be detected. Step d) can be carried out by visual examination, or by colorimetry or fluorimetry. During step d), it is possible to reveal the presence of the peptidase activity alone or in combination with other enzymatic activities.

The examples below are given by way of explanation and are in no way limiting in nature. They will make it possible to understand the invention more clearly.

EXAMPLE 1

Synthesis of Substrates

X is S

1 Synthesis of 2-(2'-aminophenyl)benzothiazole 1.1 2-(2'-Nitrophenyl)benzothiazole A mixture of 1 eq of 2-aminophenol, of ethanol and of 1 eq of 2-nitrobenzaldehyde was refluxed, using an oil bath, at a temperature at 110° C. for one hour.

The inventors left the mixture to cool to ambient temperature and recovered the precipitate by filtration. In order to recover a maximum of product, the round-bottomed flask was rinsed with the filtrate, so as to evaporate a significant portion.

The solid was dried in a desiccator under reduced pressure so as to obtain the intermediate product.

The solid obtained above was dissolved in 100 ml of dichloromethane and then 1 eq of 2,3-dicyano-5,6-dichloro-para-benzoquinone was added in small portions at ambient temperature. The reaction was carried out overnight, and then after filtration, the glassware was rinsed with DCM in order to recover the maximum of product, soluble in the DCM.

The solvent was then evaporated off under reduced pressure in order to obtain the product.

1.2 2-(2'-Aminophenyl)benzothiazole 15 g (0.15 mol) of polyphosphoric acid were placed in a 250 ml beaker and then 4.56 g (0.036 mol) of 2-aminothiophenol and 5.00 g (0.036 mol) of anthranilic acid were added. The mixture was brought to 200-220° C. for 3 hours in a sand bath with a Bunsen burner and stirred at regular intervals with a glass stirrer. The mixture was cooled slowly to 60° C. and crushed ice was added.

Next, 60 ml of water were added and the solution obtained was basified with a solution of sodium hydroxide (NaOH) until a pH of 9-10 was reached. An orange precipitate was thus obtained, which was recovered by filtration through a Buchner funnel. The solid obtained was dried and then dissolved in 50 ml of dichloromethane, and then washed 3 times with water. The organic phases were collected and then dried over $MgSO_4$ and filtered, and the solvent was then evaporated off in order to obtain the crude product. A mass of 3.01 g of a yellow/green solid was obtained after purification by column chromatography with a yield of 64%.

The data which were obtained by NMR are given below:
$^1$H NMR (270 MHz, $CDCl_3$): δ=6.40 (2H, broad s, Ar—$NH_2$), 6.75 (1H, d, J=8 Hz, Ar—H), 6.78 (1H, t, J=7 Hz, Ar—H), 7.23 (1H, t, J=7 Hz, Ar—H), 7.35 (1H, t, J=7 Hz, Ar—H), 7.46 (1H, t, J=7 Hz, Ar—H), 7.71 (1H, d, J=8 Hz, Ar—H), 7.87 (1H, d, J=8 Hz, Ar—H), 7.97 (1H, d, J=7 Hz, Ar—H).

2 Synthesis of 2-(L-alanyl-2'-amidophenyl)benzothiazole (Substrate 17)

2.1 Mixed Anhydride Method

A mass of 1.51 g (0.008 mol) of Boc-Ala-OH was dissolved in 10 ml of dry tetrahydrofuran and a $CaCl_2$ trap was added to the neck of the round-bottomed flask in order to make it impermeable. The mixture was stirred magnetically, and the temperature was reduced to −15° C. using a bath of frozen ice mixed with NaCl salts. Once this temperature had been reached, the mixture was stirred for a further 5 minutes. 1.01 g (0.010 mol) of N-methylmorpholine were then added, with great care being taken to ensure that the temperature had redescended to −15° C. before carrying out the next step. 1.09 g (0.008 mol) of isochlorobutyl formate were then added dropwise with the greatest care; the mixture became cloudy as expected with each drop added.

1.36 g (0.006 mol) of 2-(2'-aminophenyl)benzothiazole were then dissolved in the minimum amount of dry THF, and added to the mixture. The ice bath was removed after 2 hours and the mixture was stirred overnight.

The solution was filtered, the round-bottomed flask was rinsed with normal THF, and the filtrate was conserved.

The solution was then transferred, using a pasteur pipette, into a 400 ml beaker containing ice, water, and also sodium carbonate ($Na_2CO_3$). The solution was then stirred for two hours, until a clear solution was obtained. The solution was then filtered in a small Buchner funnel and the precipitate was then dissolved in methanol in order to recrystallize it.

A mass of 0.87 g of OF37A, a beige/brown powder, was obtained, with a yield of 37%.

The data which were obtained by NMR are given below:
$^1$H NMR (270 MHz, $CDCl_3$): δ=1.42 (9H, s, C—$CH_3$x3), 1.57 (3H, d, J=7.92 Hz, $CH_3$—CH—), 3.50 (1H, s, NH—Ar), 4.52 (1H, qt, NH—CH—$CH_3$), 4.51 (21H, d, NH—CH), 7.18 (1H, t, J=7.42 Hz, Ar—H), 7.44 (1H, t, J=7.42 Hz, Ar—H), 7.48 (1H, t, J=7.42 Hz, Ar—H), 7.49 (1H, t, J=7.42 Hz, Ar—H), 7.87 (1H, d, J=7.92 Hz, Ar—H), 7.92 (1H, d, J=7.92 Hz, Ar—H), 8.14 (1H, d, J=7.92 Hz, Ar—H), 8.82 (1H, d, J=7.92 Hz, Ar—H).

2.2 Deprotection

A mass of 0.30 g (0.00075 mol) of the compound to be deprotected was placed in a round-bottomed flask fitted with a $CaCl_2$ trap, and 7 ml of trifluoroacetic acid were added. The mixture was stirred magnetically overnight.

The TFA was evaporated off so as to obtain 0.35 g of OF38A in the form of a trifluoroacetic acid salt, a beige/brown powder having a yield of 88%.

The data which were obtained by NMR are given below:
$^1$H NMR (270 MHz, DMSO): δ=1.62 (3H, d, J=7.42 Hz, $CH_3$—CH—), 4.35 (1H, sx, $NH_2$—CH—$CH_3$), 5.31 (2H, broad s, $NH_2$), 7.37 (1H, t, J=7.8 Hz, Ar—H), 7.53 (1H, t, J=7.8 Hz, Ar—H), 7.61 (1H, t, J=7.8 Hz, Ar—H), 7.62 (1H, t, J=7.8 Hz, Ar—H), 8.02 (1H, d, J=7.42 Hz, Ar—H), 8.12 (1H, d, J=7.42 Hz, Ar—H), 8.20 (1H, d, J=7.42 Hz, Ar—H), 8.31 (2H, Ar—H+NH).

m.p.: 150-154° C.

3 Synthesis of 2-(L-alanyl-2'-amido-5'-chlorophenyl)benzothiazole (Substrate 19)

3.1 2-(2'-Nitro-5'-chlorophenyl)benzothiazole

A mixture of 1.18 g (0.0094 mol) of 2-aminothiophenol and 1.74 g (0.0094 mol) of 5-nitro-3-chlorobenzaldehyde in ethanol (150 ml) was refluxed for 2 hours. After having been cooled to ambient temperature, the solution was concentrated under reduced pressure. The remaining solid was diluted in a mixture of water and ethyl acetate (500 ml), and the aqueous phase was extracted a further two times using ethyl acetate (2×500 ml). The combined organic phases were dried ($MgSO_4$), filtered and concentrated in order to obtain the crude product, which was recrystallized from ethanol. A mass of 0.66 g of OF31A, a brown solid, was obtained with a yield of 25%.

The data which were obtained by NMR are given below:
$^1$H NMR (270 MHz, $CDCl_3$): δ=7.55 (4H, m, Ar—H), 7.79 (1H, d, J=2 Hz, Ar—H), 7.90 (1H, s, Ar—H), 8.10 (1H, d, J=8 Hz, Ar—H).

3.2 2-(2'-Amino-5'-chlorophenyl)benzothiazole

A mixture of 0.65 g (0.00223 mol) of 2-(2'-nitro-5'-chlorophenyl)benzothiazole OF31A and 2.52 g (0.01118 mol) of $SnCl_2.2H_2O$ in 100 ml of ethanol was heated at 70° C. for 2 hours. A verification step using thin layer chromatography showed that the mixture no longer contained any starting reactant.

After having allowed the mixture to cool to ambient temperature, the solution was poured into a beaker containing ice. The pH was adjusted to a slightly basic pH (pH 7-8) by adding an aqueous solution (5%) of sodium bicarbonate $NaHCO_3$, before having extracted the aqueous phase with ethyl acetate.

The aqueous phase thus obtained was carefully washed with brine (saturated aqueous solution of NaCl) and dried using sodium sulfate so as to obtain 0.31 g of OF53A, a brownish-yellow solid with a yield of 53%.

The data which were obtained by NMR are given below:
$^1$H NMR (270 MHz, $CDCl_3$): δ=6.41 (2H, broad s, Ar—$NH_2$), 6.74 (1H, d, J=9 Hz, Ar—H), 7.42 (3H, m, Ar—H), 7.67 (1H, d, J=2 Hz, Ar—H), 7.90 (1H, d, J=8 Hz, Ar—H), 7.98 (1H, d, J=7 Hz, Ar—H).

3.3 2-(Alanyl-2'-amido-5'-chlorophenyl)benzothiazole 3.3.1. Mixed Anhydride Method A mass of 0.29 g (0.00153 mol) of Boc-L-Ala was dissolved in 10 ml of dry tetrahydrofuran. A $CaCl_2$ trap was added to the neck of the round-bottomed flask in order to make it impermeable. The mixture was stirred magnetically and the temperature of the mixture was reduced to −15° C. using a bath of frozen ice mixed with NaCl salts.

Once this temperature had been reached, the mixture was stirred for a further 5 minutes. 0.19 g (0.00191 mol) of N-methylmorpholine was then added, with great care being taken to ensure that the temperature had redescenced to −15° C. before carrying out the next step. 0.21 g (0.00153 mol) of isochlorobutyl formate was then added dropwise with the greatest care; the mixture became cloudy as expected with each drop added. A few minutes later, a mass of 0.30 g (0.00115 mol) of 2-(2'-amino-5'-chlorophenyl)-benzothiazole was dissolved in the minimum amount of dry THF and added to the mixture. The ice bath was removed after 2 hours and the mixture was left to stir overnight.

The solution was filtered, the round-bottomed flask was rinsed with normal THF, and the filtrate was conserved. The solution was transferred, using a pasteur pipette, into a 400 ml beaker containing ice, water and also sodium carbonate ($Na_2CO_3$). The mixture was stirred for two hours, until a clear solution was obtained. The solution was filtered in a small Buchner funnel and the precipitate was then dissolved in methanol in order to recrystallize it.

A mass of 0.18 g of OF55A, a light green solid, was obtained with a yield of 36%.

The data which were obtained by NMR are given below:
$^1$H NMR (270 MHz, $CDCl_3$): δ=1.41 (9H, s, 3x$CH_3$), 1.56 (1H, d, J=7 Hz, CH—$CH_3$), 1.58 (3H, d, J=4 Hz, $CH_3$—CH), 6.45 (1H, broad s, NH), 6.74 (1H, d, J=3 Hz, Ar—H), 7.45 (3H, m, Ar—H), 7.66 (1H, d, J=3 Hz, Ar—H), 7.92 (2H, m, Ar—H).

3.3.2 Deprotection

A mass of 0.18 g (0.00042 mol) of the compound to be deprotected was placed in a round-bottomed flask fitted with a $CaCl_2$ trap, and 5 ml of trifluoroacetic acid were added. The mixture was stirred magnetically overnight.

The TFA was evaporated off so as to obtain 0.22 g of OF57A in the form of a trifluoroacetic acid salt, a sticky brown solid with a yield of 94%.

The data which were obtained by NMR are given below:
$^1$H NMR (270 MHz, DMSO): δ=1.50 (1H, d, J=7 Hz, CH—CH$_3$), 1.55 (3H, d, J=4 Hz, CH$_3$—CH), 4.80 (3H, broad s, NH$_3$), 6.87 (1H, d, J=9 Hz, Ar—H), 7.21 (1H, d, J=9 Hz, Ar—H), 7.52 (1H, m, Ar—H), 8.10 (4H, m, Ar—H).

m.p.: 124-128° C.

X is O

1 Synthesis of 2-(2'-Aminophenyl)benzoxazole

1.1 2-(2'-Nitrophenyl)benzoxazole

A mixture of 8.73 g (0.0800 mol) of 2-aminophenol, 20 ml of ethanol and 12.09 g (0.0800 mol) of 2-nitrobenzaldehyde was refluxed, using an oil bath, at a temperature of 110° C. for one hour.

The mixture was brought to ambient temperature and the precipitate was recovered by filtration. In order to recover a maximum of product, the round-bottomed flask was rinsed with the filtrate so as to evaporate a significant portion.

The solid was dried in a desiccator under reduced pressure so as to obtain 13.25 g of 2-(2'-nitrobenzylidineamino)phenol with a yield of 69%.

The solid obtained above was dissolved in 100 ml of dichloromethane, and then 12.43 g (0.0547 mol) of 2,3-dicyano-5,6-dichloro-para-benzoquinone were added in small portions at ambient temperature. The reaction was left to take place overnight, and after filtration, the glassware was rinsed with DCM in order to recover the maximum of product.

The solvent was then evaporated off under reduced pressure so as to obtain 8.39 g of 2-(2-nitrophenyl)benzoxazole, a brown-beige solid, with a yield of 64%.

The data which were obtained by NMR are given below:
$^1$H NMR (270 MHz, CDCl$_3$): δ=7.40 (1H, t, J=5 Hz, Ar—H), 7.42 (1H, t, J=5 Hz, Ar—H), 7.50 (1H, d, J=7 Hz, Ar—H), 7.72 (1H, t, J=5 Hz, Ar—H), 7.73 (1H, t, J=5 Hz, Ar—H), 7.80 (1H, d, J=7 Hz, Ar—H), 7.89 (1H, d, J=7 Hz, Ar—H), 8.15 (1H, d, J=7 Hz, Ar—H).

m.p.: 104-107° C.

1.2 2-(2'-Aminophenyl)benzoxazole

A mixture of 8 g (0.033 mol) of 2-(2'-nitrophenyl)benzoxazole and 37.58 g (0.167 mol) of $SnCl_2.2H_2O$ in 200 ml of ethanol was heated at 70° C. until the reaction was completely finished.

After having allowed the mixture to cool to ambient temperature, the solution was poured into a beaker containing ice. The pH was adjusted to a slightly basic pH (pH 7-8) by adding an aqueous solution (5%) of sodium bicarbonate $NaHCO_3$ before having extracted the aqueous phase with ethyl acetate.

The aqueous phase thus obtained was carefully washed with brine (saturated aqueous solution of NaCl) and dried using sodium sulfate so as to obtain 4.72 g of OF10C, a brownish-yellow solid, with a yield of 67%.

The data which were obtained by NMR are given below:
$^1$H NMR (270 MHz, CDCl$_3$): δ=6.20 (2H, broad s, Ar—NH$_2$), 6.78 (1H, t, J=5 Hz, Ar—H), 6.81 (1H, d, J=7 Hz, Ar—H), 7.31 (1H, t, J=5 Hz, Ar—H), 7.32 (1H, t, J=5 Hz, Ar—H), 7.34 (1H, t, J=5 Hz, Ar—H), 7.58 (1H, d, J=7 Hz, Ar—H), 7.72 (1H, d, J=7 Hz, Ar—H), 8.08 (1H, d, J=7 Hz, Ar—H).

m.p.: 100-104° C.

2 Synthesis of 2-(glycyl-2'-amidophenyl)benzoxazole (Substrate 3)

2.1 Mixed Anhydride Method

A mass of 1.40 g (0.008 mol) of N-t-Boc-Gly was dissolved in 10 ml of dry tetrahydrofuran and a $CaCl_2$ trap was added to the neck of the round-bottomed flask in order to make it impermeable. The mixture was stirred magnetically and the temperature of the mixture was reduced to −15° C. using a bath of frozen ice mixed with NaCl salts.

Once this temperature had been reached, the mixture was stirred for a further 5 minutes. A mass of 1.01 g (0.010 mol) of N-methylmorpholine was then added, with great care being taken to ensure that the temperature had redescended to −15° C. before carrying out the next step. Next, 1.09 g (0.008 mol) of isochlorobutyl formate were added dropwise with the greatest care; the mixture became cloudy as expected with each drop added.

A few minutes later, a mass of 1.26 g (0.006 mol) of 2-(2'-aminophenyl)benzoxazole was dissolved in the minimum amount of dry THF and added to the mixture. The ice bath was removed after 2 hours and the mixture was stirred overnight.

The solution was filtered, the round-bottomed flask was rinsed with normal THF and the filtrate was conserved. A slight precipitate was present. The solution was transferred, using a pasteur pipette, into a 400 ml beaker containing ice, water and also sodium carbonate ($Na_2CO_3$). The mixture was incubated for 2 hours, until a clear solution was obtained. The solution was filtered in a small Buchner funnel and the precipitate was then dissolved in methanol in order to recrystallize it.

A mass of 0.98 g of OF27A, a white powder, was obtained with a yield of 45%.

The data which were obtained by NMR are given below:
$^1$H NMR (270 MHz, CDCl$_3$): δ=1.47 (9H, s, C—CH$_3$x3), 4.05 (1H, d, J=8 Hz, —NH—CH$_2$), 4.17 (2H, d, J=8 Hz, CO—CH$_2$—NH), 5.38 (1H, broad s, Ar—NH—), 7.20 (1H, t, J=5 Hz, Ar—H), 7.40 (1H, t, J=5 Hz, Ar—H), 7.50 (1H, t, J=5 Hz, Ar—H), 7.60 (1H, t, J=5 Hz, Ar—H), 7.80 (1H, d, J=8 Hz, Ar—H), 7.85 (1H, d, J=8 Hz, Ar—H), 8.25 (1H, d, J=8 Hz, Ar—H), 8.85 (1H, d, J=8 Hz, Ar—H).

2.2 Deprotection

A mass of 0.25 g (0.00068 mol) of the compound to be deprotected was placed in a round-bottomed flask fitted with a $CaCl_2$ trap, and 7 ml of trifluoroacetic acid were added. The mixture was stirred magnetically overnight.

The TFA was evaporated off so as to obtain 0.29 g of OF30B in the form of a trifluoroacetic acid salt, a beige powder with a yield of 86%.

The data which were obtained by NMR are given below:
$^1$H NMR (270 MHz, DMSO): δ=4.05 (2H, d, J=8 Hz, CH$_2$—NH$_3$), 4.90 (3H, broad s, NH$_3$), 7.40 (1H, t, J=5 Hz, Ar—H), 7.46 (1H, t, J=5 Hz, Ar—H), 7.50 (1H, d, J=8 Hz, Ar—H), 7.70 (1H, t, J=5 Hz, Ar—H), 7.85 (1H, t, J=5 Hz, Ar—H), 8.20 (1H, d, J=8 Hz, Ar—H) 8.25 (1H, d, J=8 Hz, Ar—H), 8.40 (1H, d, J=8 Hz, Ar—H).

ESI-MS: $C_{15}H_{15}N_3O_2^+$ requires m/z 269.77 $[M+H]^+$, 226.96 $[M+H]^-$ High-resolution M.S.E.I. for $C_{15}H_{15}N_3O_2^+$. Calculated mass of molecular ion 268.1081 $[M+H]^+$. Measured mass: 268.1083 $[M+H]^+$.

m.p.: 219-222° C.

X is NX1-CO

1 Synthesis of 2-(2'-amino-5'-chlorophenyl)quinoxazol-4-one

1.1 Synthesis of 1,2-dihydro-2-(2'-nitro-5'-chlorophenyl)quinoxazolin-4-one (ref: VLS 276)

A mass of 2.31 g (0.017 mol) of 2-aminobenzamide and 3.14 g (0.017 mol) of 3-chloro-6-nitrobenzaldehyde were refluxed in ethanol for 1 hour. The mixture was then cooled, and the orange crystals obtained were harvested and dried in a desiccator at reduced pressure. A mass of 3.97 g of light orange crystals was obtained with a yield of 76% and a measured melting point of 234-236° C.

The data which were obtained by NMR are given below:
$^1$H-NMR: (DMSO) δ 6.35 (1H, t, J=2 Hz, CH), 6.70 (1H, d, J=1 Hz, Ph-H (8H)), 6.80 (1H, t, J=7 Hz, Ph-H (6H)), 7.05 s (broad), NH), 7.25 (1H, t, J=7 Hz, Ph-H (7H)), 7.65 (1H, d, d, J=6 Hz, J=1.5 Hz, Ph-H (5H)), 7.75 d, d, J=9 Hz, J=3 Hz, Ph-H (4'H)), 7.85 (1H, d, J=3 Hz, Ph-H (6'H)), 8.15 (1H, d, J=9 Hz, Ph-H (3'H)), 8.30 (1H, d (broad), NH—CO), High-resolution M.S.E.I for $C_{14}H_{10}ClN_3O_3$ Calculated mass of molecular ion 304.0483 $(M+H)^+$. Measured mass: 304.0482
$v_{max}$ cm$^{-1}$ 1661 (C=ONH), 1564 (NO$_2$), 1358 (NO$_2$), 1602 (C=N), 774 (C—Cl).

1.2 Oxidation of 2-(2'-nitro-5'-chlorophenyl)quinoxazolin-4-one (ref: VLS 278)

A mass of 9.10 g (0.03 mol) of 2-(2'-nitro-5'-chlorophenyl) quinoxazolin-4-one was dissolved in 40 ml of anhydrous acetone and was treated with 4.74 g (0.03 mol) of a solution of potassium permanganate in anhydrous acetone. This solution was added dropwise to the mixture over a period of 2-3 hours at ambient temperature. The reaction was then left to stir overnight. The excess KMnO$_4$ was eliminated by adding an excess of solid sodium bisulfite. The solution was then filtered and evaporated. A mass of 2.26 g of a pale white powder was obtained with a yield of 25% and a measured melting point of 276-278° C.

The data which were obtained by NMR are given below:
High-resolution M.S.E.I for $C_{14}H_8ClN_3O_3$ Calculated mass of molecular ion 302.0327 $(M+H)^+$. Measured mass: 304.0327. $^1$H-NMR: (DMSO) δ 7.55 (1H, t, J=7 Hz, Ph-H (7H)), 7.65 (1H, d, J=8 Hz, Ph-H (4'H)), 7.85 (1H, t, J=7 Hz, Ph-H (6H)), 7.90 (1H, d, d, J=8 Hz, J=2 Hz, Ph-H (5H)), 8.05 (1H, d, J=2 Hz, Ph-H (6'H), 8.25 (1H, d, J=8 Hz, Ph-H (3'H).
$v_{max}$ cm$^{-1}$ 3132 (NH$_2$), 3070 (NH$_2$), 1578 (NO$_2$), 1368 (NO$_2$), 1603 (NH), 1660 (CONH), 1531 (C=N), 772 (C—Cl).

1.3 Synthesis of 2-(2'-amino-5'-chlorophenyl)quinoxazol-4-one—Reduction of Compound VLS 278 (VLS 285)

A mass of 4.96 g (0.028 mol) of $SnCl_2.2H_2O$ was dissolved in a mixture of 40 ml of HCl and 5 ml of glacial acetic acid. The solution was brought to reflux at 120° C. and 1.34 g (0.0044 mol) of compound VLS 278 was added in small portions. The mixture was kept at 120° C. for half an hour and then reduced to 100° C. for 2-3 hours. A yellow solid was obtained and recovered via filtration, dissolved in water, and made basic by adding a 4M solution of NaOH. The pale yellow precipitate was harvested and dried with a desiccator under reduced pressure. A mass of 1.17 g of a yellow powder was obtained with a yield of 98% and a measured melting point of 286°-288° C.

The data which were obtained by NMR are given below:
$^1$H-NMR: (DMSO) δ 6.80 (1H, d, J=8.6 Hz, Ph-H (3'H)), 7.20 (1H, d, d, J=8.6 Hz, J=1 Hz, Ph-H), 7.30 (1H, s (broad), NH), 7.45 (1H, t, J=8 Hz Ph-H), 7.70 (1H, d J=7 Hz, Ph-H), 7.75 (1H, t, J=7 Hz, Ph-H), 7.90 (1H, d J=2 Hz, Ph-H (6'H), 8.10 (1H, d, d, J=8 Hz, J=2 Hz, Ph-H).
$v_{max}$ cm$^{-1}$ 3465 (NH$_2$), 3278 (NH$_2$), 1674 (CO), 1582 (NH), 1560 (C=N), 1159 (C—N), 766 (C—Cl).

2 Synthesis of 2-(L-alanyl-2'-amido-5'-chlorophenyl)quinoxazol-4-one (Substrate 21)

2.1 Mixed Anhydride Method (VLS 286 rep)

A mass of 0.50 g (0.002 mol) of t-Boc-L-Ala was dissolved in 10 ml of anhydrous THF. The temperature was brought to 15° C. and 0.34 g (0.0032 mol) of NMM (N methylmorpholine) was added over a period of 1 minute, followed by 0.36 g (0.00266 mol) of IBCF (isobutyl chloroformate) still at the same temperature. After this addition, the mixture was stirred for 5-10 minutes and then a solution of 0.55 g (0.002 mol) of 2 (2' amino-5' chlorophenyl)quinoxazol-4 one dissolved in the minimum amount of anhydrous THF, i.e. 5 ml, was added dropwise over a period of 2 minutes at the same temperature. The mixture was provided with an ice bath for 2-3 hours, and then left at ambient temperature overnight. The mixture was then filtered in order to remove the NMM salt, and the volume of the filtrate was reduced in order to pour it into a beaker containing water and sodium carbonate. The yellow solid was recovered and recrystallized with ethanol. A mass of 0.43 g of a yellow powder was obtained with a yield of 50% and a measured melting point of 268-270° C.

The data which were obtained by NMR are given below:
$^1$H-NMR: (DMSO) δ 1.20 (9H, s, (CH3)3C), 1.18 (1H, s (broad), NHCO), 1.40 (1H, d, J=7 Hz, CH3), 1.37 (1H, d, J=2 Hz, NH), 4.05 (1H, quartet, J=7 Hz, alaH), 7.25 (1H, t, J=7 Hz, NH—CO(CH3)3), 7.3-7.42 (2H, m, Ph-H), 7.55 (1H, t, J=7 Hz, Ph-H), 7.65 (1H, d, Ph-H (3'H)), 8.00 (1H, d, J=7 Hz, Ph-H (4'H)), 8.60 (1H, d, J=2 Hz, Ph-H), 8.65 (1H, s, Ph-H (6'H)). vmax cm-1 1668 (CONH), 1608 (NH), 1560 (C=N), 1169 (C—N), 722 (C—Cl).

2.2 Deprotection (ref: VLS 289)

The t-Boc-L-Ala derivative of 2-(2'-amino-5-chlorophenyl)quinoxazolin-4-one was deprotected by adding trifluoroacetic acid. A mixture of 0.30 g (0.0007 mol) of 2-(t-Boc-L-Ala-2'-amido-5-chlorophenyl)quinoxazolin-4-one and 5 ml of trifluoroacetic acid was mixed overnight at ambient temperature. The excess TFA was evaporated off and the brown solid thus obtained was dried using a desiccator under reduced pressure. A mass of 0.26 g (0.00057 mol) of an orangey brown solid was obtained with a yield of 81% and a measured melting point of 268-270° C.

The data which were obtained by NMR are given below:
$^1$H-NMR: (DMSO) δ 1.40 (3H, d, CH$_3$), 3.40 (1H, quartet, H-ala), 7.55 (1H, t, J=7 Hz, Ph-H), 7.67 (1H, dd, J=8 Hz, J=2

Hz, Ph-H), 7.71 (1H, d, J=8 Hz, Ph-H), 7.83 (1H, m, Ph-H), 7.90 (1H, d, J=8 Hz, Ph-H), 8.20 (1H, d, d, J=8 Hz, J=1 Hz, Ph-H), 8.30 (2H, s (broad), $NH_2$), 10.92 (1H, s (broad), NHCO). $v_{max}$ $cm^{-1}$ 1667 (CONH), 1605 (NH), 1560 (C=N), 1435 ($CH_3$), 1181 (C—N), 770 (C—Cl).

X is NX1

1 Synthesis of 2-(2'-amino-4',5'-cyclomethylenedioxyphenyl)-3-phenethyl-benzimidazole (or 2-(2'-amino-4',5'-methylenedioxyphenyl)-3-phenylethyl-benzimidazole)

1.1 Synthesis of 2-(2'-nitro-4',5'-cyclomethylenedioxyphenyl)-3-phenylethylbenzimidazole (or 2-(2'-nitro-4',5'-methylenedioxyphenyl)-3-phenylethylbenzimidazole)

1.1.1 N-Phenylethyl-2-nitroaniline (ref: VLS 209)

A mass of 4.8 g (0.04 mol) of 2-phenylethylamine was added dropwise, at ambient temperature, to a mixture of 5.6 g (0.04 mol) of 2-fluoronitrobenzene and 11.06 g (0.08 mol) of anhydrous potassium carbonate in 30 ml of DMSO. The mixture was heated at 100° C. for 3 hours. The mixture was then cooled to ambient temperature and was added to 100 ml of water, which led to the precipitation of a light orange compound. The solid was recovered by filtration and dried using a desiccator at reduced pressure. A mass of 9.4 g of orange crystals was obtained with a yield of 98%. The melting point found was coherent with the theoretical value, i.e. 64-66° C.

The data which were obtained by NMR are given below:
$^1$H-NMR: ($CDCl_3$) δ 3.00 (2H, t, J=7 Hz, —$CH_2$—), S 3.55 (2H, t, J=7 Hz, —$CH_2$—), δ 6.65 (1H, m, Ph-H), S 6.85 (1H, dd, J=8 Hz, J=2 Hz, Ph-H), S 7.20-7.50 (6H, m, Ph-H), S 8.10 (1H, s (broad), NH), δ 8.20 (1H, dd, J=8 Hz, J=2 Hz, Ph-H).

1.1.2 N-Phenylethyl-1,2-diaminobenzene (ref: VLS 210)

A solution of 0.38 g (0.01 mol) of sodium borohydride was added to a suspension of 0.52 g (0.002 mol) of copper acetylacetonate in ethanol, with magnetic stirring under nitrogen at ambient temperature. 2.42 g (0.01 mol) of the nitro compound VLS209 in ethanol were added to this solution, followed by 0.76 g (0.02 mol) of sodium borohydride in ethanol. The mixture was left stirring overnight under nitrogen at ambient temperature. The mixture was then concentrated in order to remove the excess ethanol, and water was added. An extraction step was then carried out with 2×20 ml of DCM, and the organic phase was washed several times with water, dried using potassium carbonate and concentrated on a rotary evaporator. A mass of 1.69 g of a dark oily liquid, which subsequently solidified, was obtained, with a yield of 80%. The melting point found was coherent with the theoretical value, i.e. 42-44° C.

The data which were obtained by NMR are given below:
$^1$H-NMR ($CDCl_3$) δ 2.95 (2H, t, J=7 Hz, —$CH_2$—), δ 3.27 (2H, s (broad), $NH_2$), δ 3.38 (2H, t, J=7 Hz, —$CH_2$), δ 6.69 (3H, m, Ph-H), δ 6.82 (1H, m, Ph-H), δ 7.10-7.40 (5H, m, Ph-H).

1.1.3 2-(2'-Nitro-4',5'-cyclomethylenedioxyphenyl)-3-phenethyl-benzimidazole (ref: VLS 213) (or 2-(2'-nitro-4',5'-methylenedioxyphenyl)-3-phenylethylbenzimidazole)

8.60 g (0.014 mol) of oxone (potassium monopersulfate) were added, over a period of 15 minutes at ambient temperature, to a solution of 5.08 g (0.024 mol) of N-phenylethyl-1,2-diaminobenzene, of 4.8 g (0.024 mol) of 6-nitropiperonal in 25 ml of DMF and of 1 ml of water, with magnetic stirring. The mixture was cooled with a bath of water since the reaction was exothermic, and left to stir overnight. Water was then added to the mixture and two consecutive extractions with DCM were carried out. The combined organic phases were washed with water several times, dried ($MgSO_4$) and concentrated so as to give the yellow/brown-colored crude product. Recrystallization with ethanol was carried out in order to purify the compound. A mass of 6.19 g of brown crystals was obtained with a yield of 67% and a measured melting point of 162-164° C.

The data which were obtained by NMR are given below:
High-resolution M.S.E.I for $C_{22}H_{17}N_3O_4$ Calculated mass of molecular ion 388.1292 $(M+H)^+$. Measured mass: 388.1297. $^1$H-NMR: ($CDCl_3$) δ 3.10 (2H, t, J=7 Hz, —$CH_2$—), δ 4.20 (2H, t, J=7 Hz, —$CH_2$—), δ 6.02 (1H, s, Ph-H), δ 6.18 (2H, s, O—$CH_2$—O), δ 6.80 (2H, dd, J=8 Hz, J=2 Hz, Ph-H), δ 7.10-7.40 (5H, m, Ph-H), δ 7.48 (1H, m, Ph-H), δ 7.65 (1H, s, Ph-H), δ 7.80 (1H, m, Ph-H).

$v_{max}$ $cm^{-1}$ 1364 ($NO_2$), 1523 ($NO_2$), 1610 (C=N), 1152 (C—N), 1207 (C—N), 1089 (C—O), 1473 (C—H), 728 (—$CH_2$).

1.2 Synthesis of 2-(2'-amino-4',5'-cyclomethylenedioxyphenyl)-3-phenylethylbenzimidazole (or 2-(2'-amino-4',5'-methylenedioxyphenyl)-3-phenylethyl-benzimidazole)

A solution of 0.11 g (0.003 mol) of sodium borohydride was added to a suspension of 0.16 g (0.0006 mol) of copper acetylacetonate in ethanol, with magnetic stirring under nitrogen at ambient temperature. 1.07 g (0.003 mol) of the nitro compound VLS213 in ethanol were added to this solution, followed by 0.23 g (0.006 mol) of sodium borohydride in ethanol. The mixture was left to stir overnight under nitrogen at ambient temperature. The mixture was then concentrated in order to remove the excess ethanol, and water was added. An extraction was then carried out with 2×20 ml of DCM, and the organic phase was washed several times with water, dried ($K_2CO_3$) and concentrated on a rotary evaporator. A mass of 0.92 g of a brown powder was obtained with a yield of 87% and a measured melting point of 170-172° C.

The data which were obtained by NMR are given below:
High-resolution M.S.E.I for $C_{22}H_{19}N_3O_2$ Calculated mass of molecular ion 358.1550 $(M+H)^+$. Measured mass: 358.1550
$^1$H-NMR: ($CDCl_3$) δ 3.00 (2H, t, J=7 Hz —$CH_2$—), δ 4.40 (2H, t, J=7 Hz, —$CH_2$), δ 6.00 (2H, s, O—$CH_2$—O), δ 6.35 (1H, s, Ph-H (6'H), δ 6.50 (1H, s, Ph-H (3' H)), δ 7.00 (2H, m, Ph-H), δ 7.20-7.40 (5H, m, Ph-H), δ 7.55 (1H, m, Ph-H), δ 7.85 (1H, m, Ph-H).

$v_{max}$ $cm^{-1}$ 3434 (N—H), 3350 (N—H), 1618 (C=N), 1219 (C—O), 1037 (C—N), 1157 (C—N), 1495 (Ar), 1473 (Ar), 1521 (Ar), 728 (—$CH_2$—).

2 Synthesis of 2-(L-alanyl-2'-amido-4',5'-cyclomethylenedioxyphenyl)-3-phenethylbenzimidazole (Substrate 16) (or 2-(L-alanyl-2'-amido-4',5'-methylenedioxyphenyl)-3-phenylethylbenzimidazole)

A mass of 0.50 g (0.0026 mol) of t-Boc-L-alanine was dissolved in 10 ml of anhydrous DCM, and 0.54 g (0.0026 mol) of dicyclohexylcarbodiimide was added to the solution with stirring, followed by 0.35 g (0.0026 mol) of hydroxybenzotriazole. The mixture was left to stir at ambient temperature for 45 minutes and then 0.65 g (0.0019 mol) of 2-(2'-amino-4',5'-methylenedioxolanephenyl)-3-phenylethylbenzimidazole (or 2-(2'-amino-4',5'-methylenedioxyphenyl)-3-phenylethylbenzimidazole) was added, before allowing the reaction to continue overnight. The following day, the mixture was filtered through celite and the solvent was evaporated off, and then the resulting liquid was poured into a water/ice mixture. The oily precipitate thus formed was recovered, dissolved in ethyl acetate and washed several times with a 10% solution of NaHCO$_3$ and then with water. The organic phase was dried (MgSO$_4$) and concentrated. The brown solid thus obtained was deprotected by adding a saturated solution of HCl in ethyl acetate. The precipitate was stirred with a saturated aqueous solution of Na$_2$CO$_3$ and 10 ml of DCM. The organic phase was separated and dried (MgSO$_4$) and then concentrated. A mass of 0.37 g of a brown solid was obtained with a yield of 38% and a measured melting point of 80-82° C.

The compound was purified with column chromatography (silica gel), which gave a yellow/brown solid.

The data which were obtained by NMR are given below:

$^1$H-NMR: (CDCl$_3$) δ 1.30 (3H, d, J=6 Hz, ala CH$_3$), 1.50 (2H, s (broad), NH$_2$), 3.07 (2H, t, J=7 Hz, CH$_2$), 3.40 (1H, quartet, ala H), 4.45 (2H, t, J=7 Hz, CH$_2$), 6.04 (2H, s, CH$_2$O$_2$), 6.58 (1H, s, Ph-H (6'H)), 6.85 (2H, m, Ph-H (6H, 7H)), 7.15 (3H, m, Ph-H), 7.35 (2H, d, d, Ph-H (5H, 8H)), 8.10 (1H, S, Ph-H (3'H)), $\nu_{max}$ cm$^{-1}$ 1667 (C=O), 1622 (C=N), 1239 (C—O), 1152 (C—N), 728 (—CH$_2$—).

3 Synthesis of 2-(L-alanyl-2'-amidophenyl)-3-phenylethylbenzimidazole (Substrate 14, =VLS237)

2-(2'-Nitrophenyl)-3-phenylethylbenzimidazole: This substrate was synthesized in a manner analogous to the synthesis of 2-(2'-nitro-4',5'-methylenedioxyphenyl)-3-phenylethylbenzimidazole. A yield of 78% of white crystals was obtained, and a measured melting point of 128-130° C. The data which were obtained by NMR are given below:

High-resolution M.S.E.I for C$_{21}$H$_{17}$N$_3$O$_2$. Calculated mass of molecular ion 344.1394 (M+H)$^+$. Measured mass: 344.1394. $^1$H-NMR: (CDCl$_3$) δ 3.07 (2H, t, J=6.93 Hz, —CH$_2$—), 4.20 (2H, t, J=6.93 Hz, —CH$_2$—N), 6.79 (2H, dd, J=7.67 and 1.24 Hz, Ph-H), 6.85 (1H, dd, J=7.42 and 1.73 Hz, Ph-H), 7.17 (3H, m, Ph-H), 7.36 (2H, m, Ph-H), 7.47 (1H, m, Ph-H), 7.53 (1H, t, J=7.42 Hz, Ph-H), 7.63 (1H, t, J=7.92 Hz, Ph-H), 7.81 (1H, m, Ph-H), 8.17 (1H, dd, J=8.16 and 1.48 Hz, Ph-H). IR: $\nu_{max}$ cm$^{-1}$ 1520 (NO$_2$), 1358 (NO$_2$), 1454 (C=N), 1155 (C—N), 746 (—CH$_2$—).

2-(2'-Aminophenyl)-3-phenylethylbenzimidazole: This substrate was synthesized in a manner analogous to the synthesis of 2-(2'-amino-4',5'-methylenedioxyphenyl)-3-phenylethylbenzimidazole (page 26, line 28). A yield of 77% of brown powder was obtained, and a measured melting point of 130-132° C. The data which were obtained by NMR are given below:

High-resolution M.S.E.I for C$_{21}$H$_{19}$N$_3$. Calculated mass of molecular ion 314.1652 (M+H)$^+$.

Measured mass: 314.1652. $^1$H-NMR: (CDCl$_3$) δ 3.10 (2H, t, J=7.92 Hz, —CH$_2$—), δ 4.40 (2H, t, J=7.92 Hz, —CH$_2$—), δ 4.65 (2H, s (broad), NH$_2$), δ 6.80-7.90 (13H, m, Ph-H) IR: $\nu_{max}$ cm$^{-1}$ 3417 (—NH$_2$), 3400 (NH$_2$), 1616 (C=N), 1484 (C—H), 1454 (C—H), 1155 (C—N), 733 (CH$_2$), 698 (CH$_2$), 1591 (Ph), 1484 (Ph).

2-(L-Alanyl-2'-amidophenyl)-3-phenylethylbenzimidazole: This substrate was synthesized in a manner analogous to the synthesis of 2-(L-alanyl-2'-amido-4',5'-methylenedioxyphenyl)-3-phenylethylbenzimidazole (page 29, line 8). A yield of 58% of yellow/brown powder was obtained, and a measured melting point of 80-82° C.

The data which were obtained by NMR are given below:

High-resolution M.S.E.I for C$_{25}$H$_{24}$N$_4$O$_3$. Calculated mass of molecular ion 429.1921 (M+H)$^+$. Measured mass: 429.1926. $^1$H-NMR: (CDCl$_3$) δ 1.30 (3H, d, J=6 Hz, ala CH$_3$), 1.50 (2H, s (broad), NH$_2$), 3.07 (2H, t, J=7 Hz, CH$_2$), 3.40 (1H, q, J=6 Hz, ala-H), 4.45 (2H, t, J=7 Hz, —CH$_2$—) 6.04 (2H, s, —CH$_2$O$_2$—), 6.58 (1H, s, C6'-H), 6.85 (2H, m, C6-H, and C7-H), 7.15 (3H, m, Ph-H), 7.35 (2H, dd, J=7 Hz, J=2 Hz, C5-H, C8-H), 8.10 (1H, s, N—H), IR $\nu_{max}$ cm$^{-1}$ 2918 (—CH$_2$—), 2850 (CH$_3$), 1675 (C=O), 1625 (NH$_2$), 1622 (C=N), 1152 (C—N), 749 (—CH$_2$—), 1476 (Ar), 1455 (Ar), 1034 (C—N), 1365 (CH$_3$).

EXAMPLE 2

Use of Substrates of Formula I According to the Invention for Detecting a Peptidase Activity a) Synthesis of Substrates Substrate No. 1—2-(L-Alanyl-2'-amidophenyl)benzoxazole—VLS206

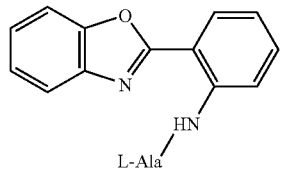

Substrate No. 2—2-(β-Alanyl-2'-amidophenyl)benzoxazole—OF22A

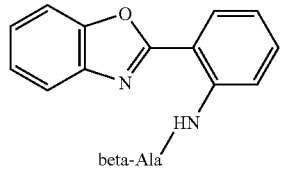

Substrate No. 3—2-(Glycyl-2'-amidophenyl)benzoxazole—OF30B

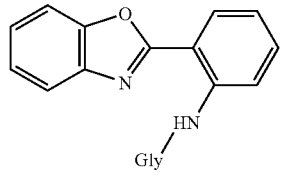

Substrate No. 4—2-(L-Alanyl-2'-amidophenyl)-5-chlorobenzoxazole—35

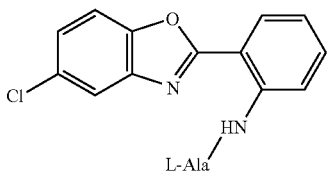

Substrate No. 11—2-(β-Alanyl-2'-amido-4',5'-dimethoxyphenyl)benzoxazole—OF24A

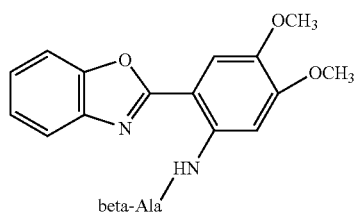

Substrate No. 17—2-(L-Alanyl-2'-amidophenyl)benzothiazole—OF38A

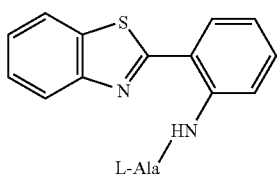

Substrate No. 18—2-(β-Alanyl-2'-amidophenyl)benzothiazole—OF33A

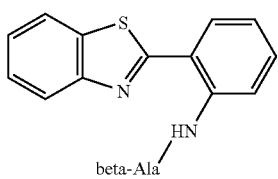

Substrate No. 19—2-(L-Alanyl-2'-amido-5'-chlorophenyl)benzothiazole

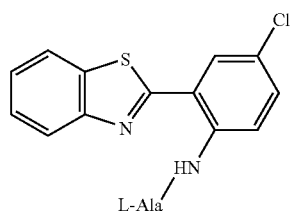

a) Substrate No. 16—2-(L-Alanyl-2'-amido-4',5'-methylenedioxolane)-3-phenyl-ethylbenzimidazole (or 2-(L-alanyl-2'-amido-4',5'-methylenedioxyphenyl)-3-phenylethylbenzimidazole)

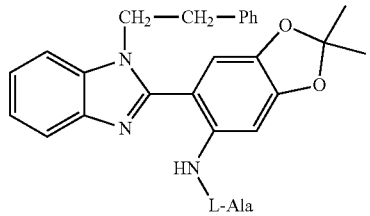

Substrate No. 14—3-(L-Alanyl-2'-amidophenyl)-3-phenylethylbenzimidazole (=VLS237)

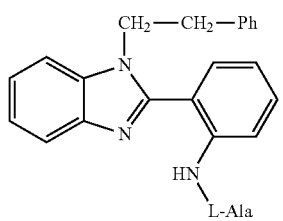

Substrates Nos. 1, 2, 4 and 11 were synthesized in a manner analogous to the synthesis of 2-(glycyl-2'-amidophenyl)benzoxazole (substrate No. 3) in Example 1.

Similarly, substrates Nos. 17 and 18 were synthesized in a manner analogous to the synthesis of 2-(L-alanyl-2'-amido-5'-chlorophenyl)benzothiazole (substrate No. 19) in Example 1.

b) Preparation of the Medium 40 mg of each substrate are dissolved in 4 ml of dimethylformamide (DMF). This solution is completely taken up in 400 ml of Columbia agar autoclaved beforehand and kept molten at 50° C. The final concentration for each substrate is therefore 100 mg/l. Each of the media is distributed into 90 mm Petri dishes in a proportion of 20 ml per dish.

c) Inoculation and Incubation 18 microorganism strains derived from collections and belonging to various species of bacteria and of yeasts are inoculated onto these media by semi-quantitative isolation of 10 µl of a suspension at 0.5 McFarland diluted to 1/20. The media are incubated for 24 hours at 37° C., and then the colonies formed are examined visually under UV illumination at 360-365 nm.

d) Reading of Results

The results obtained are given in Table 2 and Table 3.

TABLE 2

Intensity and color of the fluorescence produced by various microorganism strains in the presence of substrates according to the invention

| | Substrate according to the invention | | | | |
|---|---|---|---|---|---|
| | No. 1 (2-(L-Alanyl-2'-amidophenyl)-benzoxazole | No. 2 (2-(β-Alanyl-2'-amidophenyl)-benzoxazole | No. 3 (2-(Glycyl-2'-amidophenyl)-benzoxazole | No. 4 2-(L-Alanyl-2'-amidophenyl)-5-chlorobenzoxazole | No. 11 2-(β-Alanyl-2'-amido-4',5'-dimethoxyphenyl)-benzoxazole |
| *Escherichia coli* NCTC 10418 | ++[1] blue | + green | ++ blue | NG[2] | + blue |
| *Serratia marcescens* NCTC 10211 | ++ blue | + green | ++ blue | ++ blue | + blue |
| *Pseudomonas aeruginosa* NCTC 10662 | ++ blue | + green | +/− blue | +/− violet | +/− blue |
| *Burkholderia cepacia* 1222 | − | + green | + blue | − | + blue |
| *Yersinia enterocolitica* NCTC 11176 | ++ blue | +/− green | +/− blue | + blue | +/− blue |
| *Salmonella Typhimurium* NCTC 74 | ++ blue | − | − | NG | + blue |
| *Enterobacter cloacae* NCTC 11936 | ++ blue | + green | ++ blue | + blue | + blue |
| *Providencia rettgeri* NCTC 7475 | ++ blue | +/− green | ++ blue | + blue | + blue |
| *Bacillus subtilis* NCTC 9372 | − | NG | +/− green | NG | − |
| *Enterococcus faecalis* NCTC 775 | +/− blue | +/− green | − | +/− blue | +/− blue |
| *Enterococcus faecium* NCTC 11047 | +/− blue | +/− green | NG | − | +/− blue |
| *Staphylococcus epidermidis* NCTC 11047 | − | − | NG | − | − |
| *Staphylococcus aureus* NCTC 6571 | + green | − | + green | − | + blue |
| *Staphylococcus aureus* NCTC 11939 | + green | − | + green | − | − |
| *Streptococcus pyogenes* NCTC 8306 | − | NG | NG | − | − |
| *Listeria monocytogenes* NCTC 11994 | +/− green | ε green | +/− green | − | +/− blue |
| *Candida albicans* ATCC 90028 | − | − | NG | − | − |
| *Candida glabrata* NCPF3943 | − | − | NG | − | − |

| | Substrate according to the invention | | |
|---|---|---|---|
| | No. 17 2-(L-Alanyl-2'-amidophenyl)-benzothiazole | No. 18 2-(β-Alanyl-2'-amidophenyl)-benzothiazole | No. 19 2-(L-Alanyl-2'-amido-5'-chlorophenyl)-benzothiazole |
| *Escherichia coli* NCTC 10418 | + blue | ++ yellow | + blue |
| *Serratia marcescens* NCTC 10211 | + blue | ++ yellow | − |
| *Pseudomonas aeruginosa* NCTC 10662 | + yellow | ++ yellow | − |
| *Burkholderia cepacia* 1222 | + yellow | NG | − |
| *Yersinia enterocolitica* NCTC 11176 | + yellow | NG | NA |
| *Salmonella Typhimurium* NCTC 74 | NG | NG | +/− blue |
| *Enterobacter cloacae* NCTC 11936 | + blue | NG | + blue |
| *Providencia rettgeri* NCTC 7475 | + blue | NG | + blue |
| *Bacillus subtilis* NCTC 9372 | NG | NG | − |
| *Enterococcus faecalis* NCTC 775 | NG | NG | − |
| *Enterococcus faecium* NCTC 11047 | NG | NG | − |
| *Staphylococcus epidermidis* NCTC 11047 | NG | NG | NG |

TABLE 2-continued

Intensity and color of the fluorescence produced by various microorganism strains in the presence of substrates according to the invention

| | | | |
|---|---|---|---|
| Staphylococcus aureus NCTC 6571 | NG | NG | – |
| Staphylococcus aureus NCTC 11939 | NG | NG | – |
| Streptococcus pyogenes NCTC 8306 | NG | NG | NG |
| Listeria monocytogenes NCTC 11994 | NG | NG | – |
| Candida albicans ATCC 90028 | NG | NG | NG |
| Candida glabrata NCPF3943 | NG | NG | NG |

[1]fluorescence intensity, – = no fluorescence detected, e = trace of fluorescence, +/– = weak fluorescence, + = medium fluorescence, ++ = strong fluorescence
[2]NG = No Growth

TABLE 3

Growth, color and fluorescence produced by various microorganism strains in the presence of substrates according to the invention

| | Substrate 16 | | Substrate 14 | |
|---|---|---|---|---|
| | G | F | G | F |
| Escherichia coli NCTC 10418 | + | ++ blue | + | – |
| Serratia marcescens NCTC 10211 | + | ++ blue | + | +/– purple |
| Pseudomonas aeruginosa NCTC 10662 | + | – | + | – |
| Burkholderia cepacia 1222 | + | ++ blue | + | – |
| Yersinia enterocolitica NCTC 11176 | + | – | + | – |
| Salmonella typhimurium NCTC 74 | ++ | ++ blue | ++ | – |
| Citrobacter freundii 46262 (wild) | + | ++ blue | + | – |
| Morganella morganii 462403 (wild) | + | + blue | + | – |
| Enterobacter cloacae NCTC 11936 | + | ++ blue | + | +/– purple |
| Providencia rettgeri NCTC 7475 | + | ++ blue | + | – |
| Bacillus subtilis NCTC 9372 | + | – | + | – |
| Enterococcus faecails NCTC 775 | + | – | + | – |
| Enterococcus faecium NCTC 7171 | + | – | + | – |
| Staphylococcus epidermidis NCTC 11047 | + | – | + | – |
| Staphylococcus aureus NCTC 6571 | + | – | + | – |
| MRSA NCTC 11939 | + | – | + | – |
| Streptococcus pyogenes NCTC 8306 | + | – | + | – |
| Listeria monocytogenes NCTC 11994 | + | – | + | – |
| Candida albicans ATCC 90028 | + | – | + | – |
| Candida glabrata NCPF 3943 | +/– | – | +/– | – |

G: growth - Co: color - F: fluorescence

Contrary to what is observed with substrates based on 7-amino-4-methylcoumarin (AMC), such as L-alanine-7-AMC, for all the substrates according to the invention that were tested, the fluorescence was localized at the colony only or in the immediate vicinity.

For substrates 1, 2 and 3, for which only P differs (L-alanine, β-alanine and glycine, respectively), the intensity and/or the color of the fluorescence produced by the same strain differed. With substrate 1, all the Gram-negative bacterial strains (with the exception of the Burkholderia cepacia strain) produced a strong blue fluorescence. The two enterococcal strains produced a weak blue fluorescence and the two Staphylococcus aureus strains produced a medium green fluorescence. On the other hand, the B. cepacia strain produced a medium blue fluorescence with substrate 3 and a green fluorescence with substrate 2.

These results also indicated that the color of the fluorescence, its intensity and the toxicity varied when P is constant but X and/or R2 varied. This was the case between substrates 1, 4, 17 and 19. Thus, with substrate 4, the Pseudomonas aeruginosa strain produced a weak violet fluorescence and for the S. aureus strains, no fluorescence was detected. Substrate 17 inhibited all the Gram-positive bacterial strains and the yeasts, and with substrate 19, the P. aeruginosa strain was negative.

Similarly, there are large differences in color of fluorescence (in emission wavelength), in intensity and in toxicity between substrates 2, 11 and 18 for which P is β-alanine.

e) Conclusion

Depending on the desired application, P, X, R2 or R1 should be defined.

For example, substrate 1 (2-(L-alanyl-2'-amidophenyl) benzoxazole) makes it possible to distinguish between Gram-negative bacteria (intense blue fluorescence), yeasts and Gram-negative bacteria, and, among the latter, to distinguish enterococci (weak blue fluorescence) and S. aureus (medium green fluorescence) from the others. Substrate 3 also makes it possible to distinguish Gram-negative bacteria (blue fluorescence) from the other microorganisms.

Substrate 19 makes it possible to separate certain enterobacteria (Escherichia coli, Salmonella, Enterobacter, Morganella and Providencia) from the other microorganisms.

Other substituents, in particular the use of other peptides, can make it possible to separate other groups of microorganisms. Depending on the X, R1 and R2 groups, it is possible to vary both the color and the intensity of the fluorescence, the sensitivity or the specificity of the detection of the microorganism groups, or even the toxicity. These variations are very useful, in particular in the case of combinations with other enzyme substrates.

The invention claimed is:
1. An enzyme substrate for detecting peptidase activity of formula (I) below:

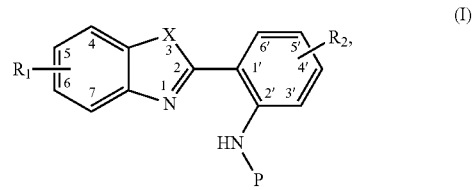

in which:
X is S, NX1, or O;
R1 is nothing or is Cl, Br, F, I, OH, or an alkyl, aryl or carboxyl group;

R2 is nothing or is Cl, O—CH$_2$—O, O—CH$_3$, F, diethylenediamine-CH$_3$, NR3R4, Br, I, OH, an alkyl, aryl or carboxyl group, NO$_2$, or

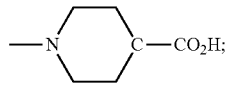

X1 is H, C$_2$H$_4$Ph, OH, an alkyl group, or an aryl group;
R3 and R4 are independently H or an alkyl group containing from 1 to 4 carbon atoms; and
P is a peptide.

2. The enzyme substrate as claimed in claim 1, in which:
X is O; and
R1 and R2 are nothing.

3. The enzyme substrate as claimed in claim 1, in which:
X is O;
R1 is Cl; and
R2 is nothing.

4. The enzyme substrate as claimed in claim 1, in which:
X is S;
R1 is nothing; and
R2 is nothing.

5. The enzyme substrate as claimed in claim 1, in which:
X is S;
R1 is nothing; and
R2 is Cl.

6. A reaction medium comprising at least one enzyme substrate as claimed in claim 1.

7. A microorganism detection and/or identification medium comprising at least one enzyme substrate as claimed in claim 1.

8. The microorganism detection and/or identification medium as claimed in claim 7, further comprising at least one other enzyme substrate specific for an enzymatic activity different from that detected by the enzyme substrate.

9. The microorganism detection and/or identification medium as claimed in claim 7, further comprising at least one other enzyme substrate specific for peptidase activity.

10. A method of detecting peptidase activity of a microorganism, the method comprising:
incubating a biological sample with an enzyme substrate; and
detecting peptidase activity if a microorganism having peptidase activity is present in the biological sample,
wherein the enzyme substrate for detecting peptidase activity is of formula (I) below:

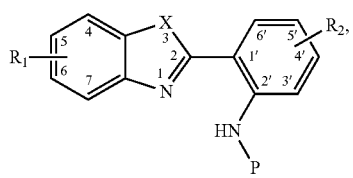 (I)

in which:
X is S, NX1, or O;
R1 is nothing or is Cl, Br, F, I, OH, or an alkyl, aryl or carboxyl group;
R2 is nothing or is Cl, O—CH$_2$—O, O—CH$_3$, F, diethylenediamine-CH$_3$, NR3R4, Br, I, OH, an alkyl, aryl or carboxyl group, NO$_2$, or

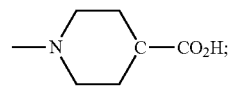

X1 is H, C$_2$H$_4$Ph, OH, an alkyl group, or an aryl group;
R3 and R4 are independently H or an alkyl group containing from 1 to 4 carbon atoms; and
P is a peptide.

11. A method of distinguishing Gram-positive bacteria from Gram-negative bacteria, the method comprising:
incubating a biological sample with the enzyme substrate as defined in claim 1; and
distinguishing Gram-positive bacteria from Gram-negative bacteria based on peptidase activity.

12. A method for detecting peptidase activity of a microorganism, the method comprising:
inoculating a microorganism detection and/or identification medium with a biological sample to be tested;
incubating the inoculated medium; and
detecting peptidase activity if the biological sample comprises a microorganism having peptidase activity,
wherein the medium comprises an enzyme substrate for detecting peptidase activity of formula (I) below:

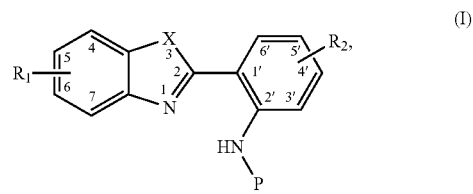 (I)

in which:
X is S, NX1, or O;
R1 is nothing or is Cl, Br, F, I, OH, or an alkyl, aryl or carboxyl group;
R2 is nothing or is Cl, O—CH$_2$—O, O—CH$_3$, F, diethylenediamine-CH$_3$, NR3R4, Br, I, OH, an alkyl, aryl or carboxyl group, NO$_2$, or

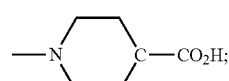

X1 is H, C$_2$H$_4$Ph, OH, an alkyl group, or an aryl group;
R3 and R4 are independently H or an alkyl group containing from 1 to 4 carbon atoms; and
P is a peptide.

13. A method for differentiating bacteria in terms of whether they belong to Gram-positive bacteria or to Gram-negative bacteria, the method comprising:
inoculating the microorganism detection and/or identification medium as claimed in claim 7 with a biological sample to be tested;
incubating the inoculated medium; and
detecting peptidase activity to differentiate bacteria as Gram-positive bacteria or Gram-negative bacteria.

14. The method as claimed in claim 10, in which:
X is O; and
R1 and R2 are nothing.

15. The method as claimed in claim 10, in which:
X is O;
R1 is Cl; and
R2 is nothing.

16. The method as claimed in claim 10, in which:
X is S;
R1 is nothing; and
R2 is nothing.

17. The method as claimed in claim 10, in which:
X is S;
R1 is nothing; and
R2 is Cl.

18. The method as claimed in claim 10, wherein a reaction medium comprises the enzyme substrate.

19. The method as claimed in claim 18, wherein the reaction medium is a microorganism detection and/or identification medium.

20. The method as claimed in claim 19, wherein the microorganism detection and/or identification medium further comprises at least one other enzyme substrate specific for an enzymatic activity different from that detected by the enzyme substrate.

21. The method as claimed in claim 19, wherein the microorganism detection and/or identification medium further comprises at least one other enzyme substrate specific for peptidase activity.

* * * * *